United States Patent
McClelland et al.

[19]

[11] Patent Number: 6,125,687
[45] Date of Patent: Oct. 3, 2000

[54] APPARATUS FOR MEASURING OUTGASSING OF VOLATILE MATERIALS FROM AN OBJECT

[75] Inventors: Gary M. McClelland, Palo Alto; Charles T. Rettner, San Jose, both of Calif.

[73] Assignee: International Business Machines Corporation, Armonk, N.Y.

[21] Appl. No.: 09/137,353

[22] Filed: Aug. 20, 1998

[51] Int. Cl.[7] .................................................. G01N 1/00
[52] U.S. Cl. ...................... 73/19.01; 73/19.12; 73/31.07; 73/863.11; 73/863.12; 422/80
[58] Field of Search ................ 73/19.01, 19.07, 73/19.12, 31.07, 24.01, 76, 73, 865.5, 38, 863.11, 863.12; 422/80

[56] References Cited

U.S. PATENT DOCUMENTS

| | | | |
|---|---|---|---|
| 4,561,286 | 12/1985 | Sekler et al. | 73/23 |
| 4,719,073 | 1/1988 | Langan | 419/1 |
| 4,735,081 | 4/1988 | Luoma et al. | 73/23 |
| 4,781,358 | 11/1988 | Langan | 266/80 |
| 4,970,891 | 11/1990 | Blevins et al. | 73/19.01 |
| 5,287,725 | 2/1994 | Zhao et al. | 73/23.2 |
| 5,408,864 | 4/1995 | Wenman | 73/38 |
| 5,442,175 | 8/1995 | Dawson | 250/288 |
| 5,569,837 | 10/1996 | Hinaga | 73/19.01 |
| 5,856,198 | 6/1999 | Joffe et al. | 436/100 |

*Primary Examiner*—Daniel S. Larkin
*Attorney, Agent, or Firm*—Lumen Intellectual Property Services

[57] ABSTRACT

An apparatus for measuring material outgassed from an object. The apparatus has a chamber containing the object, a condensed material detector (e.g. a quartz microbalance), a heater for heating the object and chamber, and a cooler for cooling the detector. The chamber is sealed from the ambient atmosphere and the detector is located within the chamber. The chamber may contain a vacuum or a gas at ambient atmospheric pressure. Material outgassed from the object is distributed throughout the chamber by vapor transport and is incident upon the detector, where it condenses. Since the detector is the only cooled surface in contact with the vapors, it collects nearly all the outgassed material. This provides high sensitivity to outgassing. The chamber may also include a mechanical stirring device for aiding vapor transport, or may be oriented so that a thermal convection current is established. Preferably, the chamber includes a snout for thermally isolating the detector and chamber so that a steep temperature gradient exists close to the detector surface. Alternatively, the detector has a coating with a high affinity for outgassed materials of interest. The chamber, detector, and object are at nearly the same temperature and the outgassed materials preferentially condense on the detector due to the high affinity of the coating for the outgassed materials.

18 Claims, 5 Drawing Sheets

APPARATUS FOR MEASURING OUTGASSING OF VOLATILE MATERIALS FROM AN OBJECT

FIELD OF THE INVENTION

This invention relates generally to devices for measuring the amount of volatile material that is outgassed from an object. More particularly, the invention relates to devices that measure the amount of outgassed volatile material by measuring the amount of the volatile material condensed on a surface.

BACKGROUND OF THE INVENTION

The measurement of the outgassing characteristics of materials is important in the construction of many delicate devices. Aboard satellites and other spacecraft, lenses, filters, windows, and other optical components must remain clean. Contamination of these components can be caused by outgassing of volatile materials from nearby parts. For example, plastics and lubricants are known to outgas in vacuum. The outgassed materials are deposited on nearby surfaces. The deposited materials damage components with sensitive surfaces. Therefore, it is desirable to minimize the amount of material outgassed in proximity to sensitive components. The amount of outgassing present is usually limited by cleaning parts and by carefully selecting the materials of which the satellite is made.

Computer hard drives can also be damaged by outgassing and recondensation of volatile materials. Volatile materials outgassed from internal hard drive components recondense on the magnetic data storage surfaces. These contaminants can be swept up by the slider that carries the read-write head, causing it to crash into the disk surface, resulting in failure of the drive and loss of data. The contaminants can also alter the frictional forces between the disk and the slider, possibly preventing the disk from rotating. Therefore, it is desirable to minimize the amount of outgassed volatile materials in the drive. This is accomplished by only using low-emission materials in the manufacturing of parts and by carefully cleaning parts prior to assembly. In selecting the materials and/or parts that can be used in the hard drive, it is necessary to measure the outgassing characteristics of candidate parts and materials.

Measurement of outgassing characteristics has typically been performed by placing the part in question in a vacuum chamber and evacuating the chamber. A pressure or mass detector is also placed within the chamber. Material outgassed from the part is detected by the sensor. A disadvantage of measuring outgassing in a vacuum is that it is time consuming to measure outgassing of many different objects because the vacuum must be reestablished each time a different object is placed within the vacuum chamber.

A problem with other techniques for measuring outgassing is that they do not intrinsically integrate the quantity of outgassed material. They must electronically integrate signals to obtain the total amount of outgassed material, which is less accurate. Further, they do not provide a sample of the outgassed material for chemical or physical analysis. These problems are present in outgassing detectors that detect the concentration of outgassed material in the vapor or gas phase and do not collect the outgassed material.

U.S. Pat. No. 4,561,286 to Sekler et al. discloses a piezoelectric contamination detector that compensates for changes in temperature that can otherwise interfere with contamination measurements. Sekler does not disclose the use of the device in a chamber for measuring the amount of material outgassed from an object.

U.S. Pat. No. 4,735,081 to Luoma et al. discloses a detector for detecting vapors in gaseous fluids, such as air. The air is passed over a detector having a crystal oscillator with a coating selected to absorb the vapor of interest. Luoma does not disclose the measurement of outgassed materials from an object in a closed chamber.

U.S. Pat. No. 5,408,864 to Wenman discloses a method of measuring the amount of gas desorbed from a solid. The solid is placed in a chamber with a specially designed gas. The pressure in the chamber is measured as a function of temperature. The absorptive properties of the solid are then determined from this measurement. Wenman's method requires accurate measurement of pressure inside the chamber. Wenman's method does not use condensed material detectors.

U.S. Pat. Nos. 4,781,358 and 4,719,073 to Langan disclose an apparatus and method for monitoring parts in a sintering furnace. Langan monitors the outgassing of the parts as they are being sintered. Langan flushes the furnace with gases as the parts are sintered.

U.S. Pat. No. 5,287,725 to Zhao et al. discloses an apparatus for detecting volatile material on the surface of a semiconductor wafer. The wafer is placed in a vacuum chamber and heated while the walls of the chamber are cooled. The apparatus is rather inefficient, detecting only a small portion of the material evaporated from the wafer.

OBJECTS AND ADVANTAGES OF THE INVENTION

It is a primary object of the present invention to provide a device for measuring the amount of outgassing from an object that:

1) does not require operation in a vacuum environment, and can be operated at atmospheric pressure;
2) assures that a large portion of the material outgassed from the object is detected, and therefore is naturally integrating, which provides a high sensitivity and accurate calibration for the outgassed material;
3) collects the outgassed material, making it available for further chemical or physical analysis;
4) can be used to measure the quantity of material on the surface of an object; and
5) is relatively simple in design, construction and operation.

These and other objects and advantages will be apparent upon reading the following description and accompanying drawings.

SUMMARY OF THE INVENTION

These objects and advantages are attained by an apparatus having a chamber containing an object to be measured for outgassing, a condensed material detector, and a means for establishing a temperature difference between the object and the detector so that the object is hotter than the detector. The detector is exposed to the interior of the chamber so that material outgassed by the object is incident on the detector. The detector is cooler than the object so the outgassed material may condense on the detector. The detector may be cooled by a refrigerator, and the object may be heated by an electric heater.

The chamber may contain a gas at any pressure from vacuum to atmospheric pressure or above. The outgassed material may reach the detector by diffusion. The chamber may or may not be sealed from the ambient atmosphere. If the chamber contains a gas at a pressure greater than about 1 Torr, the apparatus may be oriented so that thermal convection currents are established by the temperature difference to increase the rate of transport of outgassed material to the detector. The apparatus may also include a stirring device for increasing the rate of transport of the outgassed materials from the object to the detector. The gas in the chamber may be any relatively inert gas, such as nitrogen, noble gases, or even air.

The apparatus preferably includes a snout that extends from the chamber to the detector. A tip of the snout close to the detector is preferably made to be thermally insulating.

The chamber is preferably made of weakly adsorbing material such as glass, polytetrafluoroethylene, stainless steel, or gold-plated copper.

Preferably, the object and the chamber are in thermal contact so that they are at the same temperature. Also preferably, the temperature difference between the object and detector is in the range of about 50–150 degrees Celsius. Also, it is preferred for the chamber to be hotter than the detector.

The apparatus may also include an additional collecting surface for collecting outgassed material, so that the detector does not collect all the outgassed material from the object.

Also, the detector may have a coating with a high affinity for outgassed material from the object.

Alternatively, the present invention includes an embodiment where the detector and the object are at nearly the same temperature (i.e. within 50 degrees Celsius). The detector has a coating with a high affinity for outgassed material from the object and so collects the outgassed material without needing to be held at a temperature lower than the temperature of the object.

DETAILED DESCRIPTION

The present invention provides an apparatus for measuring the amount of material outgassed from an object. The measurement is performed by causing the outgassed material to travel by vapor transport from the outgassing object to a condensed material detector, where the outgassed material collects. The outgassed material preferentially collects on the detector because the detector is held at a temperature lower than the object, or because the detector is selected to have a higher affinity for the outgassed material, or both. The vapor transport can occur over a very wide range of pressures (e.g., from vacuum to above atmospheric pressure) and is preferably aided by thermal convection or mechanical stirring.

Figure 1A:
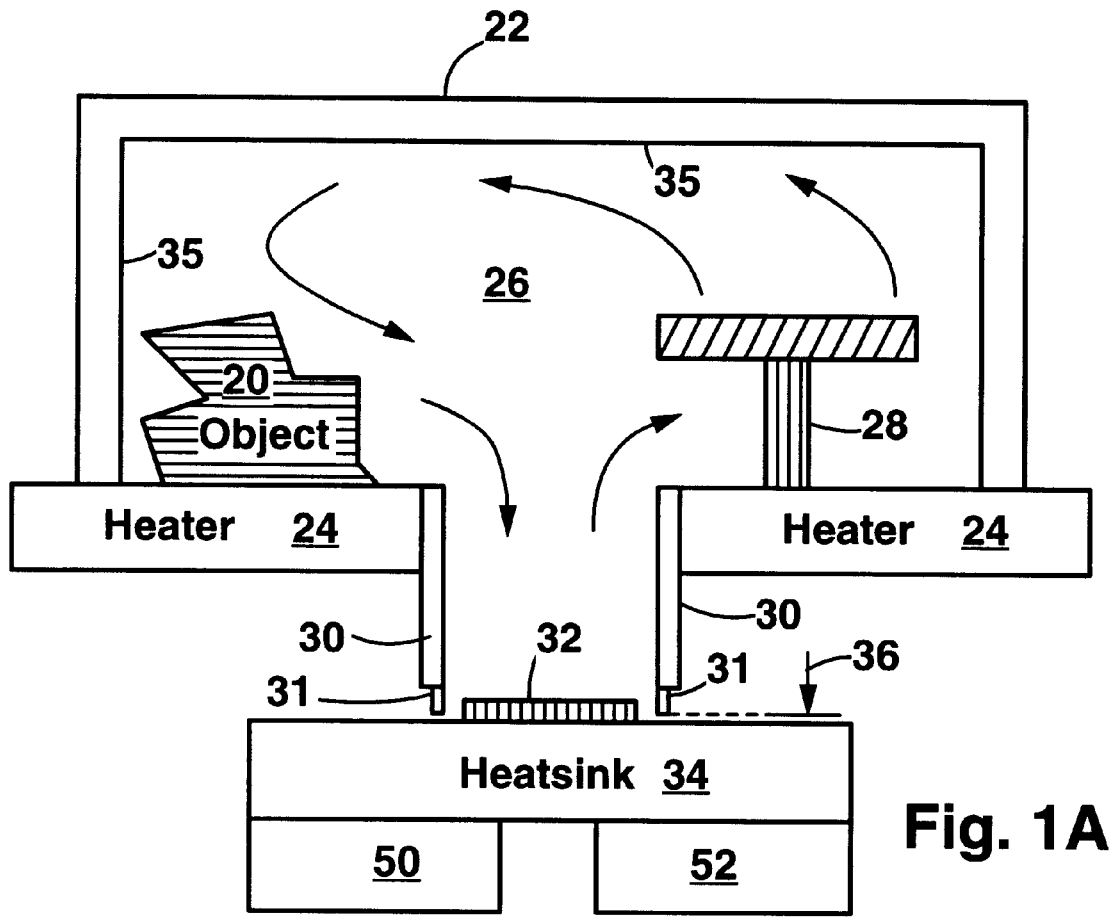
FIG. 1A shows a preferred embodiment of the apparatus of the present invention.

FIG. 1A shows a specific preferred embodiment of the present invention. An object 20 to be measured for outgassing is located within a chamber 22. The object is in good thermal contact with a heater 24 that heats the object 20. The chamber contains a gas 26 at atmospheric pressure. The gas 26 is circulated throughout the chamber 22 by a stirring device such as a fan 28. A snout 30 has an opening directed toward a condensed material detector such as a surface acoustic wave device or resonant quartz microbalance 32. The microbalance 32 is located on a heatsink 34 such that the microbalance is maintained at a temperature cooler than the temperature of the object 20. The heatsink may be water cooled, air cooled, or cooled by an active refrigerator 52. The heatsink may also have a purge heater 50 for periodically heating the microbalance 32 in order to purge collected material. Preferably, the chamber 22 is also heated in addition to the object 20.

The snout 30 and heatsink 34 preferably do not form an airtight seal. A gap 36 between the snout and heatsink may be a few thousandths of an inch (e.g. about 0.001–0.003 inches). Therefore, the gas 26 in the chamber is at ambient atmospheric pressure. However, the chamber is not substantially open to the ambient atmosphere. The chamber tends to maintain the same gas within it during operation of the apparatus. The gas 26 may be pure air, dry nitrogen, or any other relatively inert gas. The apparatus may include a supply of gas so that the gas 26 in the chamber 22 may be periodically purged. Also, the apparatus may be purged by opening the chamber to the atmosphere while heating. The gas 26 may be purged between outgassing measurements of different objects 20, for example.

Preferably, the chamber is made of a relatively inert material such as stainless steel, TEFLON, or glass. These materials have the beneficial property of having surfaces that have a low affinity for many common outgassed materials. Copper can also be used, but should be gold-plated to suppress oxidation at elevated temperatures. The chamber must be made of materials that can tolerate elevated temperatures above about 100 degrees Celsius.

In operation, the heater 24 heats the object 20 and the heatsink 34 cools the microbalance 32. The object 20 is hotter than the microbalance 32. Preferably, the heater 24 also heats the chamber 22 and snout such that the snout 30, chamber 22, and object 20 are all hotter than the heatsink 34 and microbalance 32. Material outgassed from the object 20 is condensed on the cool microbalance 32, where it is detected and measured. The outgassed material does not collect on the chamber surfaces 35 because the chamber 22 is hot and is weakly adsorptive. The snout 30 causes a steep temperature gradient to exist close to the microbalance 32. The steep temperature gradient helps the outgassed material to be preferentially deposited on the microbalance 32.

Preferably, a tip portion 31 of the snout 30 is made of a thermally insulating material such as quartz so that heat is not conducted between the snout 30 and heatsink 34. Also preferably, the tip portion 31 has a thin thickness of less than 0.01 inches. The snout 30 has a thickness 60 of about 0.05 inches. The thin thickness of the tip 31 provides a high thermal resistance between the heatsink 34 which is cold and the chamber 22 and snout 30 which are hot. The high thermal resistance of the tip 31 helps provide a steep temperature gradient just above the surface of the microbalance 32. The snout 30 should be as short as possible while still maintaining the steep temperature gradient.

The fan 28 circulates the gas 26 around the object 20 and helps to reduce the time necessary for the outgassed material to travel from the object 20 to the microbalance 32. Volatile material outgassed from the heated object is mixed into the circulating gas 26. The volatile material is condensed on the surface of the microbalance 32 and is thereby detected and measured. The volatile material is not deposited on the inside surfaces 35 of the chamber 22 because the chamber is held at an elevated temperature and is made of a weakly adsorptive material. Almost all the volatile material outgassed from the object is deposited on the microbalance 32. Alternatively, molecular diffusion (with no active mixing by fan 28) of outgassed material from the object 20 to the microbalance 32 can be relied upon for transport, but is not preferred since it results in a slow time response.

The low affinity of the chamber surfaces 35 for the outgassed material results in the outgassed material preferentially condensing on the detector. Preferably, the chamber has a low surfaces area for the volume enclosed, and has a sufficiently low affinity for the outgassed material such that at least about 80% of the material outgassed by the object is collected on the detector (the rest is collected on the surfaces 35 of the chamber). Also it is preferable for the residence time of the outgassed material on the surfaces 35 (determined in large part by the material of the chamber surfaces) to be shorter than the time scale of the measurement (i.e. shorter than about 10–60 minutes).

Since almost all the material outgassed from the object 20 is deposited onto the microbalance 32, the apparatus of the present invention is readily calibrated and is sensitive to small quantities of material outgassed from the object 20. The microbalance is also naturally sensitive to small amounts of deposited material. In a specific example, the microbalance has a resonant frequency of about 6 MHz and changes in resonant frequency by 100 Hz for each microgram of material deposited on the microbalance surface. The apparatus can therefore detect substantially less than 1 microgram of material outgassed from the object.

The heater 24 and heatsink 34 produce a temperature difference between the object 20 and microbalance 32. The temperature difference results in a difference in the degree of saturation of the vapor of the outgassed material at the object and microbalance. In particular, the degree of saturation of the outgassed material at the microbalance is high enough for condensation to occur. The temperature difference must be selected to result in outgassing at the object 20 and condensation at the microbalance 32. As a specific example, for organic materials, the partial pressure of the outgassed material at the temperature of the microbalance can be about $10^{-2}$ Torr and at the temperature of the object, the partial pressure can be greater than about 1 Torr. These conditions will result in organic materials being outgassed from the object 20 and condensed on the microbalance 32. It is noted these partial pressures will not be reached in actual practice because the gas 26 is being actively mixed. These partial pressure differences can be used to select temperatures for the object and microbalance for a given species of outgassing material. If the vapor pressure of the material to be detected is known as a function of temperature, then the object and microbalance temperatures can be selected to result in outgassing and condensation of the material at the object and microbalance, respectively. For many volatile materials, temperature differences in the range of about 50–150 Celsius are appropriate. In order to avoid condensation of water vapor, the detector temperature should be at room temperature or above. In the absence of water vapor, the detector could be cooled below room temperature.

After a measurement is performed, the microbalance is heated by the purge heater 50 while the chamber is open, being pumped on, or being purged with gas, and the volatile outgassed materials are evaporated from the microbalance 32. It is known in the art that microbalances yield inaccurate measurements when a large amount of material is deposited on the microbalance surface. Heating the microbalance prepares it to perform another measurement by causing the condensed material to evaporate. This heating process can also be used to characterize the outgassed material. A thermal analysis spectrum of the outgassed material can be obtained by heating the microbalance slowly with the chamber open (or while vacuum pumping on the chamber) and monitoring the signal loss as a function of temperature. For a mass-sensitive detector (e.g. the microbalance), this spectrum will provide a means for thermal gravimetric analysis. The temperature at which material leaves is a function of how strongly the material is bound to the microbalance. For example, lower vapor pressure materials will evaporate at a higher temperature. The thermal analysis spectrum may also be a useful way to distinguish small amounts of outgassing material in the presence of large amounts of another material that evaporates at a different temperature. It is noted that this method of generating a thermal analysis spectrum is effective with other types of real-time condensed material analysis. Examples include mass spectrometers used in temperature-programmed desorption (TPD) measurements and microbalances used in thermal gravimetric analysis (TGA) measurements.

Also, the temperature of the object and chamber can be increased gradually during the outgassing process. This results in different species of outgassed material to be outgassed at different times. Therefore, the different species can be distinguished. This method is useful for detecting the presence of a small amount of one outgassed species in the presence of another.

It is noted that the time response of the apparatus is affected by the volume enclosed by the chamber 22. In order to have a fast time response, the chamber should be constructed to fit the object 20, with a minimum of excess volume.

Figure 1B:
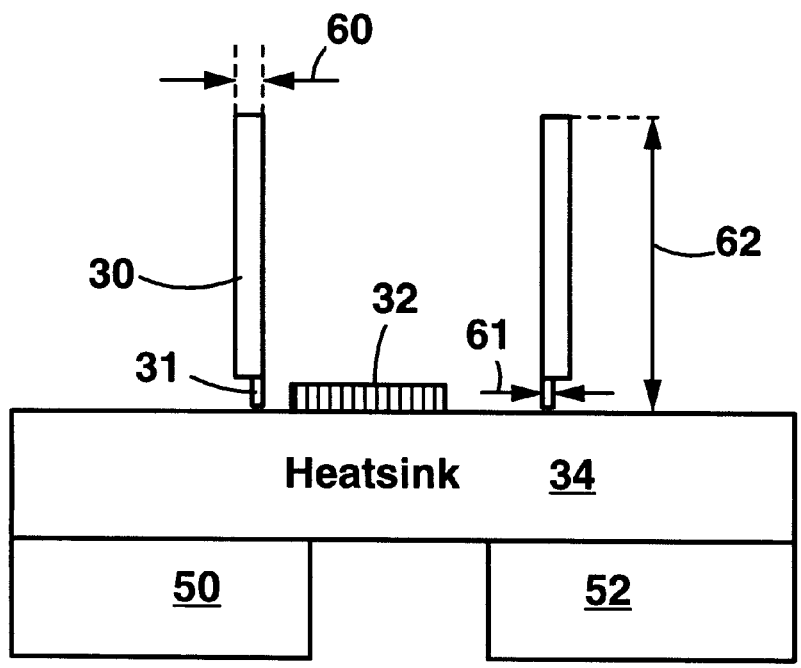
FIG. 1B shows a closeup view of a snout as used in the embodiment of FIG. 1.

FIG. 1B shows a closeup view of the snout 30 and snout tip 31. The snout has a wall thickness 60 and a length 62. If the snout 30 is in thermal contact with the heatsink 34, the temperature of the microbalance 32 may rise to the point where the outgassed material no longer condenses on the microbalance 32. In addition, the snout 30 itself may be cooled to a point where outgassed material is condensed on the snout surfaces. Both effects result in a reduction of detected material and a corresponding loss of sensitivity of the apparatus. For these reasons, the snout 30 and snout tip 31 should be made of material with a low thermal conductivity. Use of a thermally insulating snout tip 31 also results in a steep thermal gradient close to the microbalance 32. Preferably, the thermal conductance of the snout tip 31 is less than about 0.01 watt/Kelvin. This low conductance of the snout tip 31 can be accomplished by using a thin wall thickness to impede heat flow. The thickness 61 of the snout tip 31 is less than about 0.01 inches, and is more preferably less than about 0.002 inches. Possible materials for the snout 30 and snout tip 31 include quartz and stainless steel. The length 62 of the snout 30 should be as short as possible while still allowing a large temperature difference between the chamber and microbalance 32.

Alternatively, the tip portion 31 and snout 30 are the same thickness. In this case, the snout 30 and tip 31 should both be made of a thermally insulating material.

Figure 2:
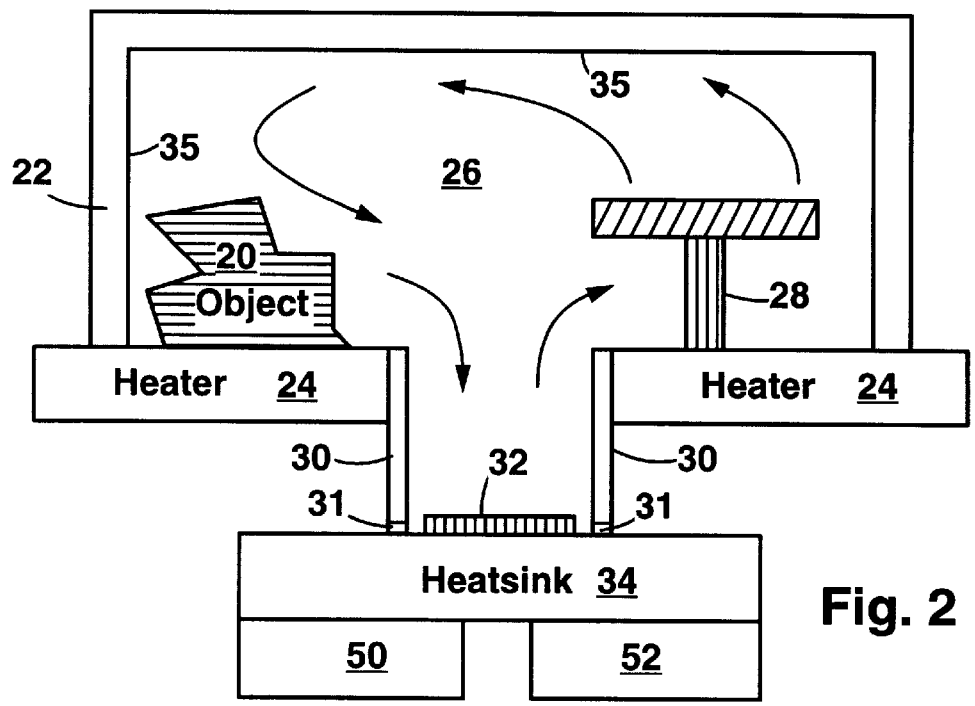
FIG. 2 shows an embodiment in which the snout is in direct contact with a heat sink.

The present invention includes the possibility of sealing the chamber airtight against the ambient atmosphere (i.e. forming an airtight seal between the heatsink 34 and snout 30). Such an embodiment is shown in FIG. 2. Here, the snout 30 is made of a material with a low thermal conductivity such that the heatsink 34 is not excessively heated by the snout 30. Alternatively, only the snout tip 31 is made of a thermally insulating material (e.g., quartz). The pressure of the gas 26 inside the chamber can be greater or less than ambient pressure. Preferably, the pressure of the gas 26 inside the chamber is sufficient to enable the fan 28 to circulate the gas 26. The gas pressure should be at least about 1 Torr (and is preferably greater) for the fan to be useful in this regard.

Figure 3:
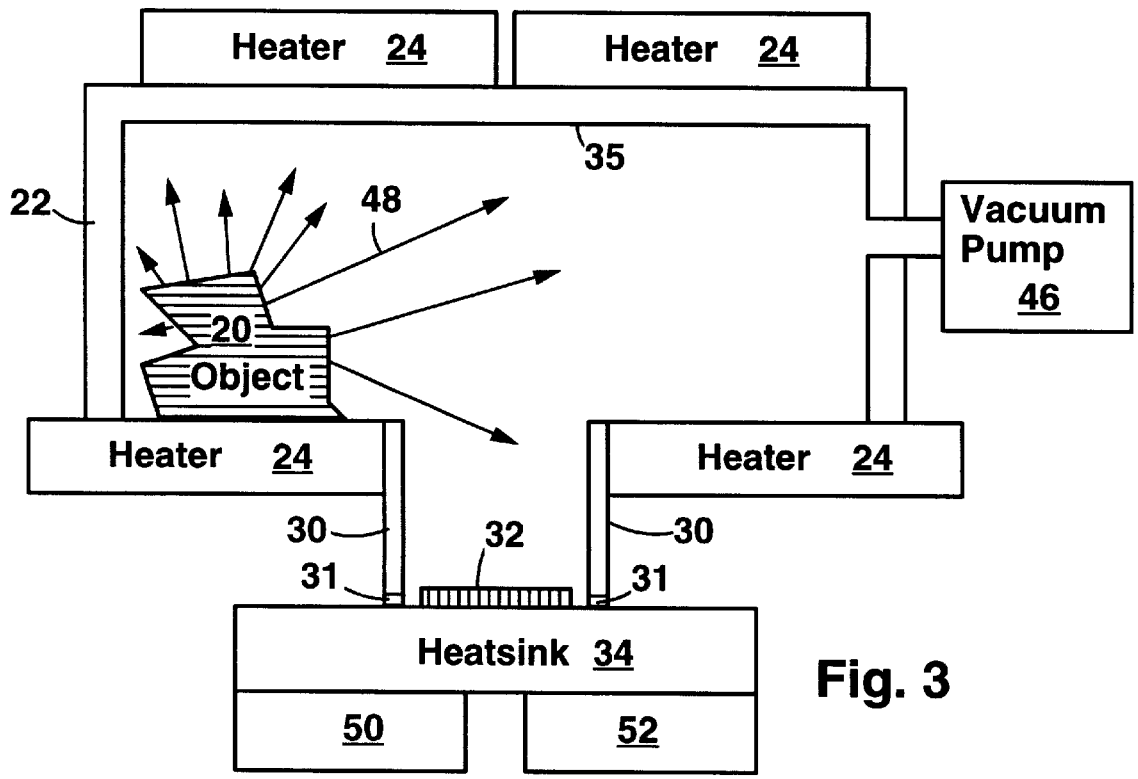
FIG. 3 shows an embodiment in which a chamber contains a vacuum.

FIG. 3 shows an embodiment in which the shout 30 and heatsink 34 are sealed airtight and the chamber contains a vacuum provided by a vacuum pump 46. Outgassed material from the object 20 typically follows straight-line paths 48 (i.e. molecular flow), which generally intersect the inside chamber surface 35. The outgassed material incident upon surfaces 35 is re-outgassed from the surfaces 35 (which are hot) and is eventually incident upon the microbalance 32, where the outgassed material condenses. It is noted that operating the apparatus with a vacuum quickens the response time because the outgassed material takes less time to reach the detector. The response time quickens as pressure is reduced until the mean free path of particles in the chamber becomes comparable to the size of the chamber. An apparatus with a small chamber volume will have a faster minimum attainable response time (all other factors being equal).

It is also noted that, for maximum sensitivity, the vacuum pump 46 should not be operated while a measurement is being performed. Preferably, the chamber is pumped out, the vacuum pump is sealed off from the chamber 22, and then the measurement is performed by heating the object. Most preferably in this embodiment, the chamber volume is small and the pump 46 is fast so that the chamber can be rapidly evacuated, resulting in a minimum of outgassed material being removed by the pump 46. This is of particular concern when the chamber is maintained at a high temperature, because objects will be heated immediately after being placed in the chamber.

Preferably, the entire apparatus is placed inside a vacuum, so that the chamber contains a vacuum without being sealed vacuum tight. This is preferable because it allows for a small gap between the snout 30 and heatsink 34 so that they are better thermally insulated from one another.

Also shown in FIG. 3 is the option of actively heating substantially the entire chamber 22 with heaters 24. The chamber 22 may be made of a thermally conductive material such as copper so that the entire chamber surface 35 is hot. If copper is used for the chamber, the inside surface 35 should be plated with an inert material such as gold to prevent oxidation. In the embodiment where the chamber contains a vacuum, it is preferred to heat the entire chamber so that the outgassed material does not recondense on the chamber surfaces 35.

Figure 4A:
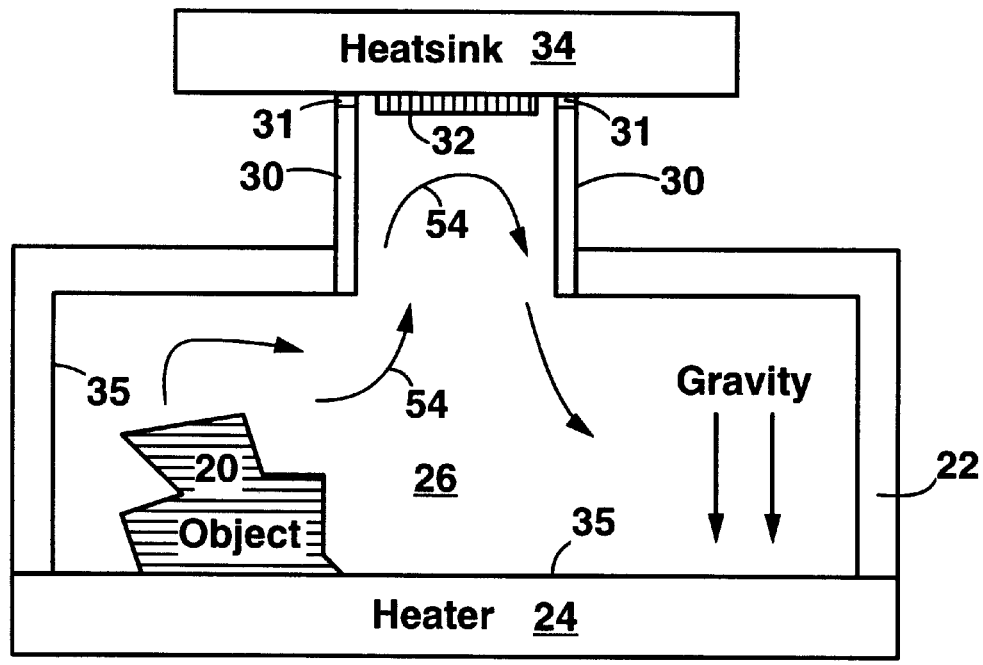
FIGS. 4A and 4B show embodiments in which the orientation of the apparatus creates thermal convection currents inside the chamber.

FIG. 4A shows an embodiment in which the chamber 22 is filled with gas 26 and circulation of the gas 26 is provided by thermal convection 54. Thermal convection is assured because the apparatus is oriented so that the microbalance and cool heatsink 34 are above the hot object 20 and heaters.

Figure 4B:
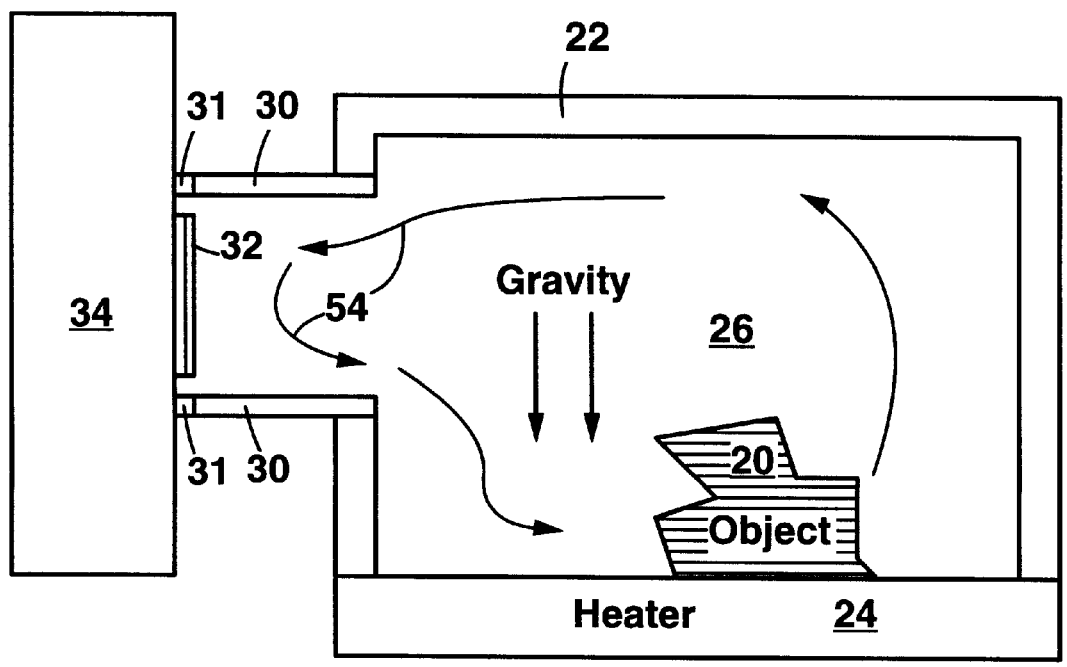

Due to the convection 54, no fan 28 is required for a relatively fast time response to be achieved. The convection efficiently cycles the gas 26 containing outgassed material past the microbalance 32, where it condenses. FIG. 4B shows another embodiment that relies on convection for transport. Here, the microbalance 32 and heatsink 34 are disposed to the side of the heater 24 and hot object 20, causing the convection 54 to be established.

Figure 5:
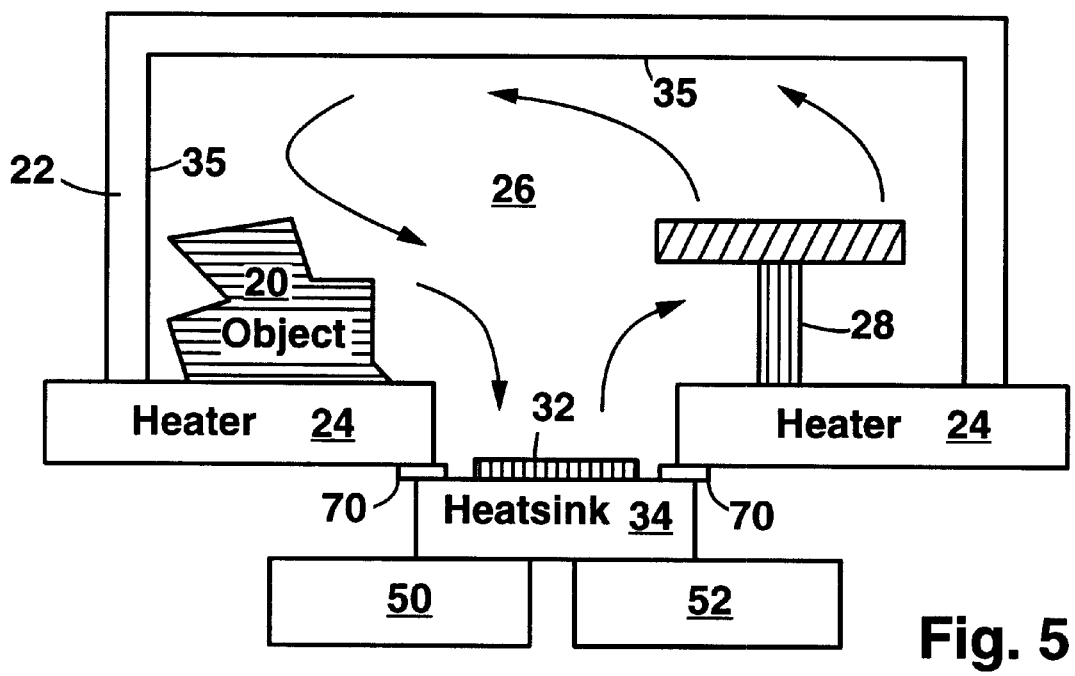
FIG. 5 shows an alternative embodiment in which the snout is not used.

FIG. 5 shows an alternative embodiment of the present invention in which the snout 30 is not used. Here, the heatsink is in contact with the heaters 24. The surface area of contact between the heaters 24 and heatsink 34 should be minimized. Also, a layer of insulating material 70 can be disposed between the heatsink 34 and the heaters 24. However, if no snout 30 is used, it is preferable to have an air gap in place of the insulating material 70. An air gap will provide good thermal isolation if the chamber is located above the heatsink. This is because no convetion currents will be formed by locating the hot chamber above the cold heatsink. It is preferable to use the snout in the present invention because it helps to maintain the temperature difference between the microbalance 32 and the rest of the apparatus.

Figure 6:
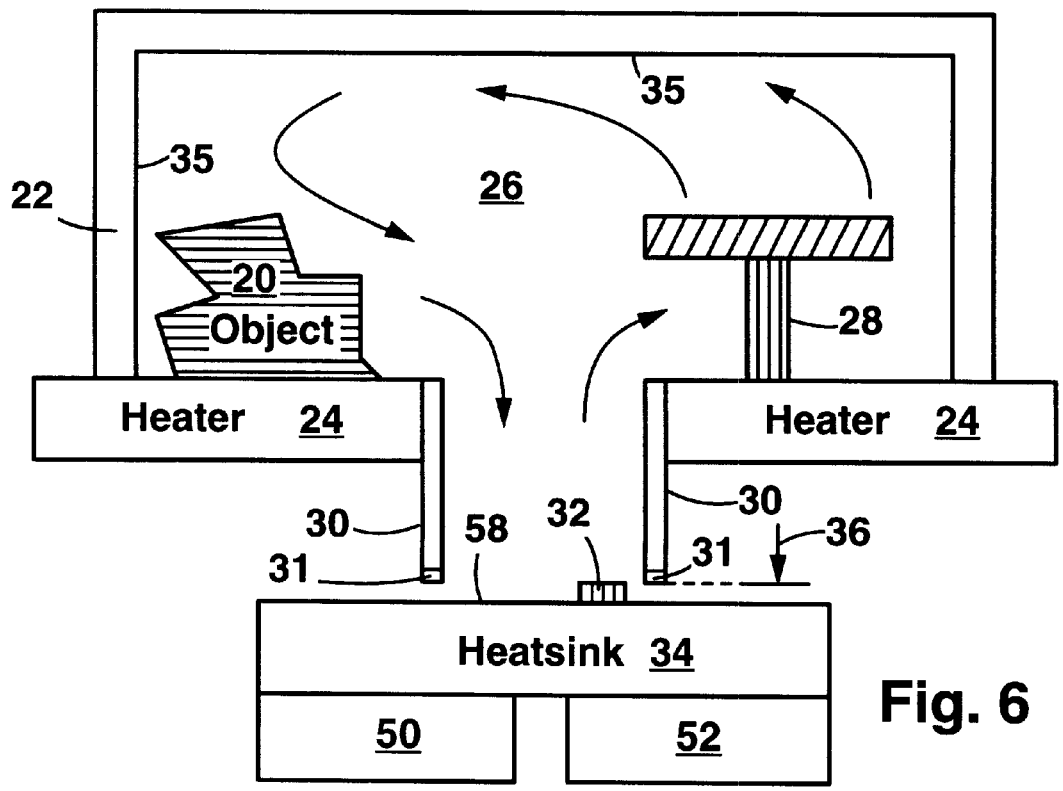
FIG. 6 shows an embodiment in which a detector does not collect all the material outgassed from an object inside the chamber.

It is known in the art that the performance of condensed material detectors can be adversely affected by excessive buildup of condensed material. For example, microbalances behave nonlinearly when overloaded with condensed material and may even cease functioning altogether. Similarly, optical-based detectors such as ellipsometers or spectrophotometers may perform poorly if performing measurements on a surface with large amounts of condensed material. For these reasons, it is desirable in some circumstances to attenuate the amount of material condensed upon the condensed material detector. FIG. 6 shows an embodiment of the present invention providing this feature. A microbalance 32 is made substantially smaller than an exposed surface 58 of the heatsink 34. The exposed surface 58 acts as an additional collecting surface. The exposed surface 58 will therefore compete with the microbalance 32 for outgassed material from the object 20. The exposed surface 58 and microbalance 32 together will capture all of the outgassed material from the object 20. The amount of material captured by each will depend upon the temperatures of the microbalance and heatsink 34 and the adsorption/absorption characteristics of the heatsink and microbalance. It is noted that the function of the exposed surface 58 an also be provided by any cooled surface (additional collecting surface) exposed to the interior of the chamber 22.

If the microbalance and additional collecting surface (e.g. exposed surface 58) have similar temperatures and adsorption/absorption characteristics, then the relative amounts of material captured by each may be proportional to their relative surface areas. In the case where the relative amounts are not proportional to the relative surface areas due to the particular transport properties of the chamber, the proportionality factor can be determined by a calibration process. In this way, overloading of the microbalance can be prevented while still allowing relatively accurate outgassing measurements.

Figure 7:
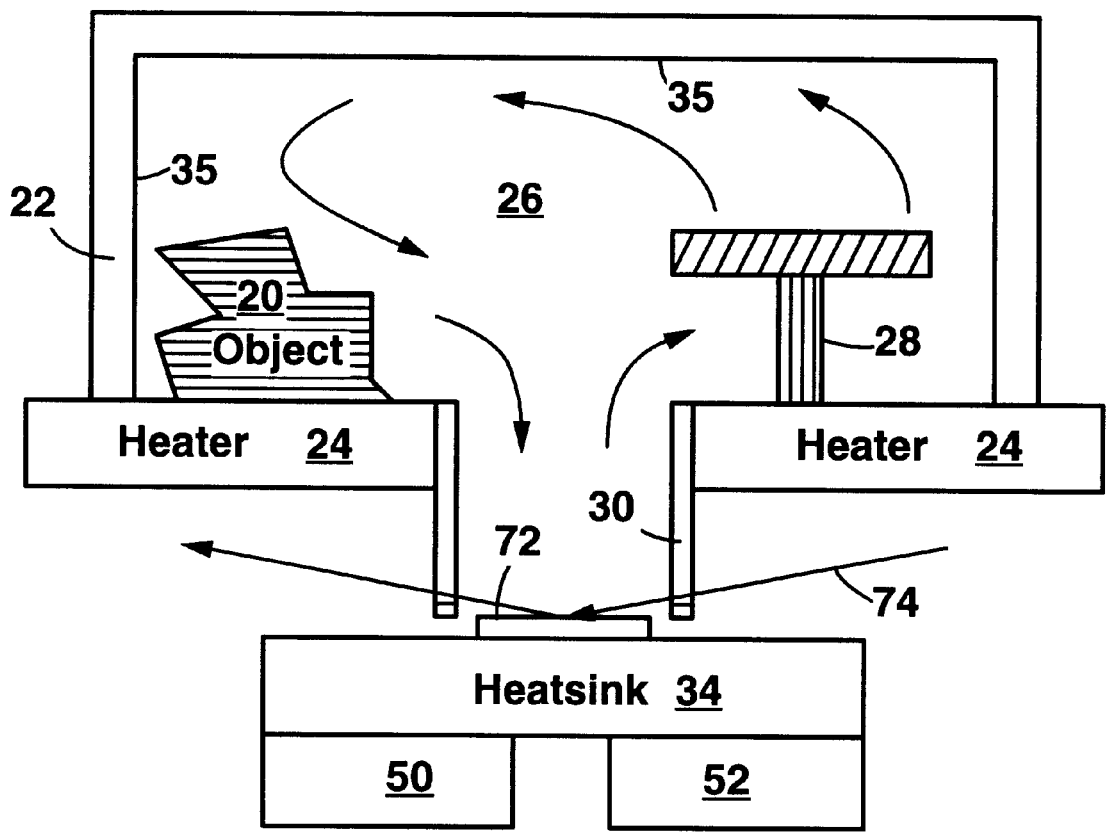
FIG. 7 shows an embodiment in which an optical based detector is used.

It is noted that the microbalance 32 is only a specific example of a condensed material detector. FIG. 7 shows an embodiment in which a substrate 72 such as a glass slide is in contact with the heatsink and a light beam 74 performs measurements on the outgassed material that condenses on the substrate 72. The snout 30 is made of transparent material. The optical measurement can include ultraviolet, visible, or infrared absorption or ellipsometry. Also, with different geometrical arrangements, light can be passed through the substrate 72 to perform measurements. Further, the substrate 72 can be removable from the apparatus.

If the pressure in the chamber is lower than about 0.01 Torr, it is possible to use an electron or ion spectroscopy technique, such as Auger spectroscopy, UV or X Ray photoemission, or secondary ion mass spectrometry, to monitor the build up of material on the substrate 72 (e.g. a glass slide). Light and charged particle spectroscopies have the advantage of being able to provide some identifying information about the material condensed, and to do so in real-time. To avoid the problem of large amounts of condensed material buildup, which might render some techniques inoperable (e.g. oscillators by quenching the oscillation, and optical detectors by absorbing all the light) the outgassed material can be condensed over a relatively wide area. This option is described with reference to FIG. 6.

It is not necessary to use a condensed material detector that responds in real time (e.g. microbalance 32) to the collection of outgassed material. Alternatively, the substrate 72 is removed from the apparatus after a measurement, and the condensed material is extracted for some other type of analysis, e.g. liquid or gas chromatography. These approaches could also be combined. For example, the microbalance 32 or substrate 72 that has monitored the mass collected during the measurement is removed after the measurement, and the chemical identity of the condensed materials on the microbalance subsequently determined by chromatography or spectroscopy.

It is noted that the condensed material detector (e.g. the microbalance 32 or substrate 72) can have a coating of a material that has a high affinity for outgassed materials to be detected. In this way, the detector can be made to be less dependent upon being properly cooled. In cases where optical, or electron, or ion spectroscopy is used, the coating can be applied to the substrate 72 at which the optical, or electron, or ion spectroscopy apparatus is directed.

Figure 8:
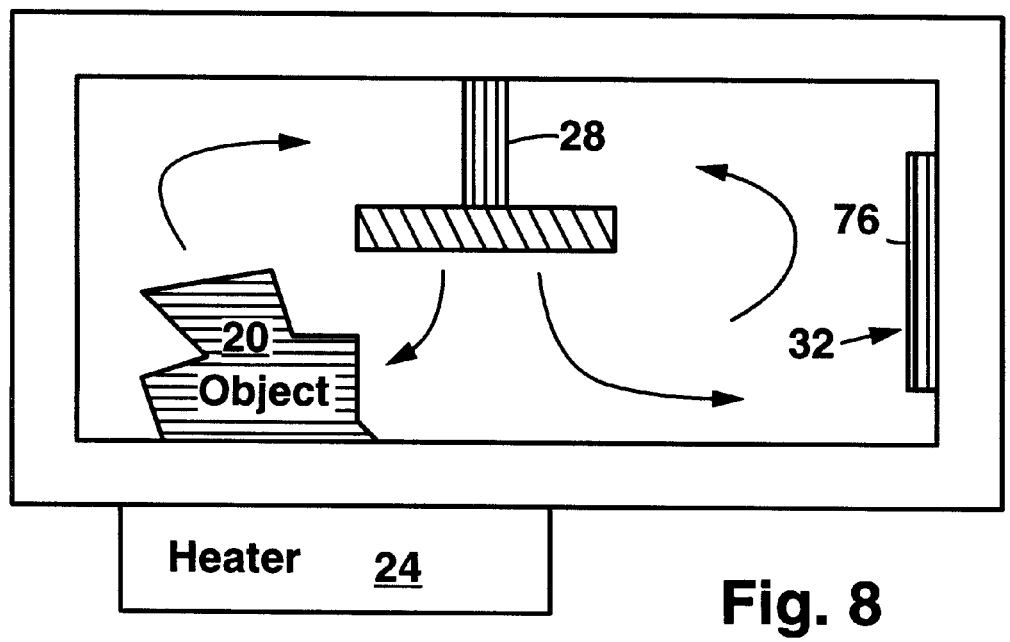
FIG. 8 shows an alternative embodiment in which the detector and object have nearly the same temperature and the detector has a coating with a high affinity for outgassed materials.

FIG. 8 shows another alternative embodiment of the present invention in which a large temperature difference between the microbalance 32 and object 20 is not necessary. In this embodiment, the snout 30 is not needed. The object 20 must be heated to a temperature that is sufficient to cause outgassing, but the microbalance does not necessarily need to be cooled. The object and the detector are at nearly the same temperature. The surface of the microbalance 32 has a coating 76 to which the outgassed material has a high affinity. The affinity can take the form of a physical or chemical interaction, and it may occur at the top most molecular layer of the detector (surface adsorption), by diffusion in into the bulk of the detector (absorption), or by collecting in the pores of a porous solid. Also, an acoustic wave device or substrate 72 may have a coating to improve the collection properties. In the case of a microbalance with a surface coating, the collected material changes the effective mass of the oscillator, changing its frequency. It may also change the Q (quality factor) of the oscillator by causing damping.

The coating 76 must have an affinity for outgassed material that is greater than the affinity of the object 20 for the outgassed material. For the purposes of this instrument, by affinity we mean the tendency of the material to bind or be adsorbed to the object or coating. This depends on the mathematical product of the outgassing material's surface (for adsorption) or volume (for absorption) with the equilibrium constant for adsorption or absorption from the gas phase. For this instrument to work, the affinities of the coating and object should be such that at equilibrium, the amount of material adsorbed or absorbed on the coating is substantially greater (preferably >5 times more) than the amount of material adsorbed or absorbed on the object. The amount of material absorbed/adsorbed on the object and coating is dependent upon the relative surface areas in addition to the relative affinities of the object and coating.

Also, the affinity of the coating 76 for the outgassed material should be greater than the affinity of the chamber surface 35 for the outgassed material. The entire apparatus (including the microbalance 32) can then be held at substantially the same temperature and the coating will absorb most of the outgassed material. However, it is generally preferable not to heat the microbalance as heat tends to liberate the outgassed material from the coating 76. As in the above embodiments, the chamber 22 can contain a gas or vacuum. The fan 28 is preferred but not necessary. Since a strong temperature gradient is not used, it is generally not possible to cause convection currents as shown in FIGS. 4A and 4B.

The coating 76 must have an affinity for outgassed material that, is greater than the affinity of the object 20 for the outgassed material. By the term "affinity", we mean adsorption and/or absorption energy. A coating with a strong affinity will have a high binding energy with the outgassed material. The affinity of the coating 76 for the outgassed material should be greater than the affinity of the chamber surface 35 for the outgassed material. The entire apparatus (including the microbalance 32) can then be held at substantially the same temperature and the coating will absorb most of the outgassed material. However, it is generally preferable not to heat the microbalance as heat tends to liberate the outgassed material from the coating 76. As in the above embodiments, the chamber 22 can contain a gas or vacuum. The fan 28 is preferred but not necessary. Since a strong temperature gradient is not used, it is generally not possible to cause convection currents as shown in FIGS. 4A and 4B.

Many different materials can be used for high-affinity coatings [1]. Specific examples of coatings include various polymers, [2] self-assembled monolayers, [3,4] organometallic materials, [5] and cavitands, [6]. Coatings can be selected systematically based on a knowledge of the chemical and physical properties of the target compound. [1] Reference can be made to the following publications concerning the selection and design of high-affinity coatings:

1. J. W. Grate and M. H. Abraham, "Solubility interactions and the design of chemically selective sorbent coatings for chemical sensors and arrays" Sensors and Actuators B, 3 (1991) 85–111.
2. K. D. Schierbaum, A. Gerlach, M. Haug, and W. Gopel, "Selective detection of organic molecules with polymers and supramolecular compounds; application of capacitance, quartz microbalance and calorimetric transducers" Sensors and Actuators A, 31 (1992) 130–137.
3. K. Matsuura, Y. Ebara, and Y. Okahata, "Guest selective adsorption from gas phase onto a functional self-assembled monolayer immobilized on a super-sensitive quartz crystal microbalance" Thin Solid Films, 273 (1996) 61–65.
4. X. C. Zhou, L. Zhong, S. F. Y. Li, S. C. Ng, H. S. O. Chan, "Organic vapor sensors based on quartz crystal microbalance coated with self-assembled monolayers" Sensors and Actuators B, 42 (1997) 59–65.
5. X. A. Battenberg, V. F. Breidt, and H. Vahrenkamp, "Synthesis and test of organometallic materials as sensitive layers on quartz microbalance devices" Sensors and Actuators B, 30 (1996) 29–34.

6. P. Nelli, E. Dalcanale, G. Faglia, G. Sberveglieri, and P. Soncini, "Cavitands as selective materials for QMB sensors for nitrobenzene and other aromatic vapors" Sensors and Actuators B, 13–14 (1993) 302–304.

The present invention is useful in any application where it is desired to measure the amount of material outgassed from an object. For example, the present invention can be used to estimate the surface area of an object, where the surface area is proportional to an amount of adsorbed material (which can be caused to outgas). Also, the present invention can be used to measure the amount of volatile material deposited on an object. The amount of lubricant coating a screw, for example, can be measured using the present invention. Also, the amount of material outgassed by parts (e.g. plastic, metal, glass, or composite parts) can be measured. This is particularly useful in selecting materials and components for contamination-sensitive applications, such as parts for use in data storage hard drives, hermetically sealed contamination-sensitive devices, or in satellites. In such applications, it is important to have accurate information about the outgassing characteristics of component parts.

It will be clear to one skilled in the art that the above embodiment may be altered in many ways without departing from the scope of the invention. Accordingly, the scope of the invention should be determined by the following claims and their legal equivalents.

What is claimed is:

1. An apparatus for measuring an amount of material outgassed from an object, the apparatus comprising:
   a) a chamber for placing the object therein, said chamber containing a gas at a pressure greater than 1 Torr;
   b) a condensed material detector in fluid communication with the interior of the chamber;
   c) a means for establishing a temperature difference between the detector and the object such that the object is hotter than the detector and such that the material outgassed from the object is condensed on the detector;
   said apparatus being oriented such that convection currents are established due to the temperature difference.

2. The apparatus of claim 1, further comprising a snout extending between the chamber and the condensed material detector.

3. The apparatus of claim 2, wherein the snout is made of a material selected from the group consisting of quartz and stainless steel.

4. The apparatus of claim 2, wherein the snout has a snout tip portion with a wall thickness less than a wall thickness of the snout, the tip portion being closer to the detector than to the chamber.

5. The apparatus of claim 4, wherein the snout tip portion has a thermal conductance less than about 0.01 watt/Kelvin.

6. The apparatus of claim 4, wherein the snout tip portion has a wall thickness less than about 0.01 inches.

7. An apparatus for measuring an amount of material outgassed from an object, the apparatus comprising:
   a) a chamber for placing the object therein, said chamber containing a gas substantially at atmospheric pressure;
   b) a condensed material detector in fluid communication with the interior of the chamber;
   c) a means for establishing a temperature difference between the detector and the object such that the object is hotter than the detector and such that the material outgassed from the object is condensed on the detector;
   said apparatus being oriented such that convection currents are established due to the temperature difference.

8. The apparatus of claim 7, further comprising a snout extending between the chamber and the condensed material detector.

9. The apparatus of claim 8, wherein the snout is made of a material selected from the group consisting of quartz and stainless steel.

10. The apparatus of claim 8, wherein the snout has a snout tip portion with a wall thickness less than a wall thickness of the snout, the tip portion being closer to the detector than to the chamber.

11. The apparatus of claim 10, wherein the snout tip portion has a thermal conductance less than about 0.01 watt/Kelvin.

12. The apparatus of claim 10, wherein the snout tip portion has a wall thickness less than about 0.01 inches.

13. An apparatus for measuring an amount of material outgassed from an object, the apparatus comprising:
   a) a chamber for placing the object therein;
   b) a condensed material detector in fluid communication with the interior of the chamber;
   c) a means for establishing a temperature difference between the detector and the object such that the object is hotter than the detector and such that the material outgassed from the object is condensed on the detector; and
   d) a snout extending between the chamber and the condensed material detector.

14. The apparatus of claim 13, wherein said apparatus is oriented such that convection currents are established due to the temperature difference.

15. The apparatus of claim 13, wherein the snout is made of a material selected from the group consisting of quartz and stainless steel.

16. The apparatus of claim 13, wherein the snout has a snout tip portion with a wall thickness less than a wall thickness of the snout, the tip portion being closer to the detector than to the chamber.

17. The apparatus of claim 16, wherein the snout tip portion has a thermal conductance less than about 0.01 watt/Kelvin.

18. The apparatus of claim 16, wherein the snout tip portion has a wall thickness less than about 0.01 inches.

* * * * *